(12) United States Patent
Bernhart et al.

(10) Patent No.: US 7,062,310 B2
(45) Date of Patent: Jun. 13, 2006

(54) CATHETER TIP ELECTRODE ASSEMBLY AND METHOD FOR FABRICATING SAME

(75) Inventors: William Henry Bernhart, Mount Joy, PA (US); John Philip Thompson, Harrisburg, PA (US); John Raymond Penica, Middletown, PA (US); Paul Steven Sremcich, Harrisburg, PA (US); John E. Hampton, Bainbridge, PA (US); Brent David Yohn, Newport, PA (US); Keith Miller, Manheim, PA (US)

(73) Assignee: Tyco Electronics Corporation, Middletown, PA (US)

( * ) Notice: Subject to any disclaimer, the term of this patent is extended or adjusted under 35 U.S.C. 154(b) by 268 days.

(21) Appl. No.: 10/679,568

(22) Filed: Oct. 6, 2003

(65) Prior Publication Data

US 2005/0075554 A1   Apr. 7, 2005

(51) Int. Cl.
*A61B 5/04* (2006.01)

(52) U.S. Cl. ...................... 600/373; 600/393
(58) Field of Classification Search ............... 600/373, 600/374, 393; 607/138, 122
See application file for complete search history.

(56) References Cited

U.S. PATENT DOCUMENTS

| | | | | |
|---|---|---|---|---|
| 3,800,800 A | * | 4/1974 | Garbe et al. ............... | 607/138 |
| 4,729,385 A | | 3/1988 | Juncosa et al. ............ | 128/734 |
| 5,370,671 A | * | 12/1994 | Maurer et al. ............. | 607/138 |
| 5,385,577 A | * | 1/1995 | Maurer et al. ............. | 607/138 |
| 5,464,448 A | * | 11/1995 | Malewicz ................... | 607/138 |
| 5,667,615 A | * | 9/1997 | Maurer et al. ............. | 607/138 |
| 6,162,184 A | | 12/2000 | Swanson et al. ........... | 600/549 |
| 6,456,863 B1 | | 9/2002 | Levin et al. ................ | 600/374 |
| 2002/0013537 A1 | | 1/2002 | Rock | |

OTHER PUBLICATIONS

Patent Abstracts of Japan, Publication No. 2001027734, Publication Date Jan. 30, 2001, Application Date Jul. 13, 1999, Application No. 11199288, Olympus Optical Co. Ltd.
International Preliminary Examining Authority: European Patent Office, Munich, "Notification of Transmittal of the International Preliminary Report on Patentability."
Jun. 12, 2005, Applicant's Reference 18092 PCT, International Application No. PCT/US2004/032885, International Filing Date May 10, 2004, Priority Date Jun. 10, 2003.

* cited by examiner

*Primary Examiner*—Lee S. Cohen

(57) ABSTRACT

An electrode assembly for a sensor catheter tip includes a first electrode and a second electrode each having a central axis. The two electrodes are axially aligned and spaced apart along the axis. Each of the first and second electrodes comprises a contact aperture spaced from the center axis, and a contact element positioned within each of the contact apertures. The center axis of each of the first and second electrodes is substantially aligned, and the contact elements corresponding to each of the first and second electrodes are offset, thereby providing staggered contact points for each respective electrode.

16 Claims, 10 Drawing Sheets

CATHETER TIP ELECTRODE ASSEMBLY AND METHOD FOR FABRICATING SAME

This invention relates generally to manufacturing of medical instruments, and, more specifically, to the manufacture of a catheter electrode assembly for an impedance spectroscopy system.

Impedance spectroscopy has been used to detect ischemia (a condition of inadequate blood flow and oxygen delivery to a given tissue) in biological tissues using different instrumental methods. Impedance spectroscopy differs from other impedance measurements (which have long been used for a variety of biomedical applications) in that it involves multiple measurements over a range of frequencies that as a whole contain significantly more information of the structural and electrical properties of the sample.

At least one known impedance spectroscopy system for monitoring tissue damage in hollow viscous organs includes a sensor catheter and an impedance spectrometer for electrically driving the catheter to obtain a complex impedance spectrum of tissue proximate the catheter. The catheter is configured to be inserted into any hollow viscous organ, and the catheter includes four Ag/AgCl electrodes positioned on an end tip of the catheter. The electrodes are coaxially spaced apart a short distance from one another, and the outer two electrodes inject current into the tissue, while the inner two electrodes measure the resulting voltage. Leads, electrically connected to the electrodes, extend along the wall of the catheter tubing or in a lumen portion of the tubing, and terminate at an interface plug suitable for electrical and mechanical connection to the impedance spectrometer. Once the catheter is in place in one of a patient's hollow viscous organs, the impedance spectrometer causes the electrodes in the tip of the catheter to inject a current into the mucosal tissue at different frequencies, allowing for the measurement of the tissue's complex impedance spectrum. Analysis of the spectrum determines the extent to which the tissue is damaged. See, for example, U.S. Patent Application Publication US 2002/0013537.

The construction of the catheter tip assembly for such a system has proven difficult in a number of aspects. The catheter tip assembly is, for example, typically inserted into the throat or nasal passage of a patient and into a gastrointestinal organ, and the therefore must be of a relatively small size and have a uniform, high quality surface finish. The tip assembly, however, includes a relatively large number of component parts which must be assembled and interconnected, including a tip, four electrodes, dielectric spacer elements between the electrodes, and leads attached to each electrode, which can make a uniform surface finish difficult to achieve. Additionally, assembly of the many component parts is cumbersome, and separately connecting the electrical leads to the spaced electrodes in a reliable manner is difficult. Managing the wire leads in the constrained internal space of the assembly, which entails threading the wires through the dielectric spacer elements, is especially difficult. These and other difficulties not only complicate the tip assembly time and increase manufacturing costs, but may negatively affect the performance and reliability of the impedance spectroscopy system when treating critically ill patients.

BRIEF DESCRIPTION OF THE INVENTION

In one embodiment, an electrode assembly for a sensor catheter tip is provided. The assembly includes a first electrode and a second electrode each having a central axis. The two electrodes are axially aligned and spaced apart along the axis. Each of the first and second electrodes comprises a contact aperture spaced from the center axis, and a contact element positioned within each of the contact apertures. The center axis of each of the first and second electrodes is substantially aligned, and the contact elements corresponding to each of the first and second electrodes are offset, thereby providing staggered contact points for each respective electrode.

Optionally, the contact elements of the first and second electrode are offset approximately 90 degrees from one another. Each of the first and second electrodes comprise a disk defined by multiple regions, the contact element positioned in one of the regions, the other of the regions comprising a lead aperture extending therethrough. Each of the contact elements have an axial length which is different for each of the contact elements, and each contact element comprises a tail portion configured for soldering or crimping. An overmolded dielectric spacer element is disposed between the first and second electrodes, and the dielectric spacer element extends at least partially through one of the electrodes.

In another embodiment, a catheter tip assembly for an impedance spectroscopy system is provided. The assembly comprises a rounded dielectric tip, and a first electrode disk adjacent the tip which comprises a body having a contact aperture therethrough. A second electrode disk is axially spaced from the first electrode disk, and the second electrode comprises a body having a contact aperture therethrough. The second electrode disk is rotated relative to the first electrode disk about a longitudinal axis so that the contact apertures are circumferentially offset from one another.

In another embodiment, a method of fabricating a catheter tip for an impedance spectroscopy system is provided. The catheter tip includes a plurality of electrodes with a dielectric material positioned between adjacent electrodes. Each of the electrodes includes a contact aperture and at least one lead aperture, and the electrodes are electrically connected to respective contacts. The method comprises positioning one of the contacts in contact with each of the electrodes via the respective contact apertures, stacking the electrodes and attached contacts, and rotating each electrode relative to the adjacent electrode in the stack so that the contacts are offset from one another in the stack.

DETAILED DESCRIPTION OF THE INVENTION

Figure 1:
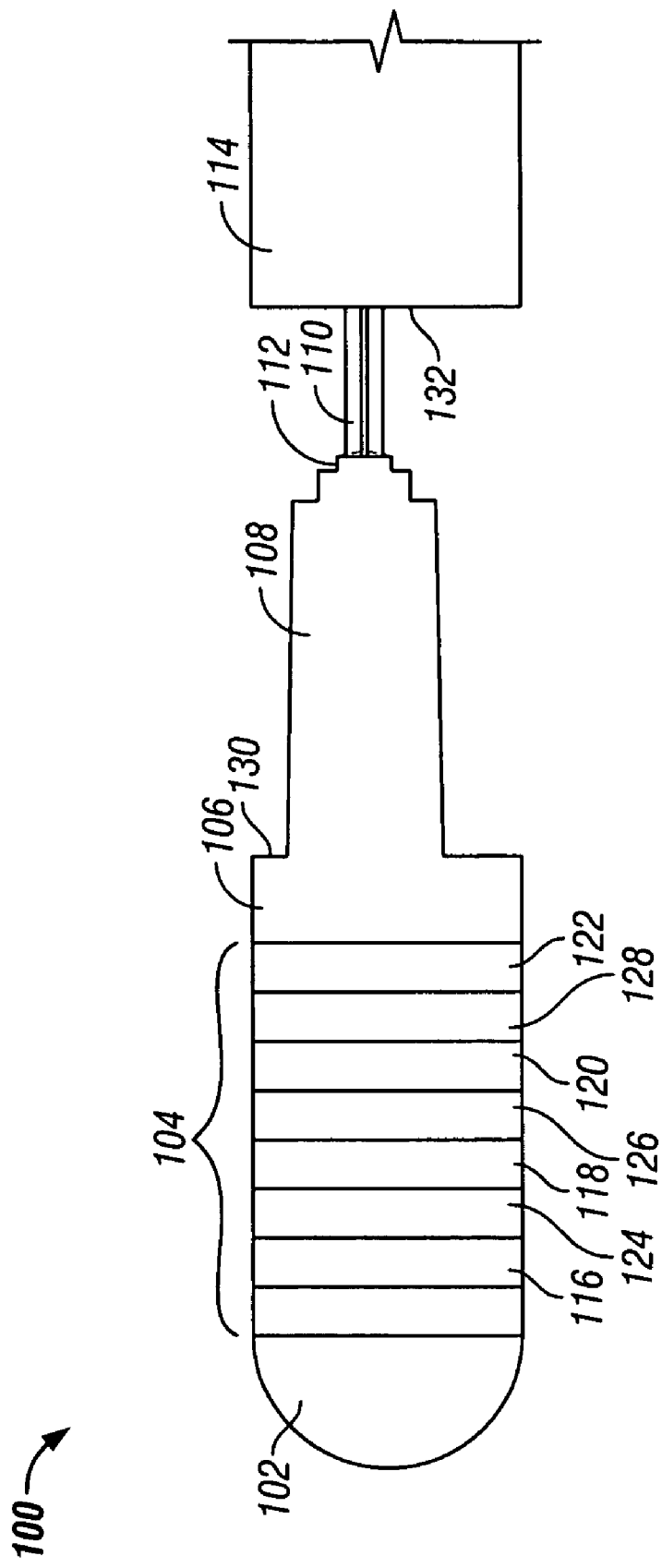
FIG. 1 is a plan view of an exemplary tip assembly formed in accordance with an exemplary embodiment of the present invention and adapted for use in a sensor catheter assembly for an impedance spectroscopy system.

FIG. 1 illustrates a tip assembly 100 for a sensor catheter of an impedance spectroscopy system. The tip assembly 100 comprises a hemi-spherically rounded tip 102, an electrode assembly 104 extending from the tip 102, a connector portion 106 extending from the electrode assembly 104 opposite the tip 102, and a coupler portion 108 extending from the connector portion 106. As described in detail below, in a preferred embodiment, the tip assembly 100 is fabricated in a series of molding operations which ensures reliable electrical interconnection of the electrode assembly 104 with a relatively few number of parts in comparison to known catheter tip assemblies. Performance and reliability of the tip assembly 100 may therefore be provided at a reduced cost.

In an exemplary embodiment, the electrode assembly 104 of the tip assembly 100 includes four generally cylindrical electrodes 116, 118, 120 and 122 which are electrically connected, via respective wires 110 (two of which are shown in FIG. 1) to the impedance spectroscopy system. Stacking and rotating of the electrodes, 116 through 122, as described below, provides staggered or offset contact points (not shown in FIG. 1) for each lead wire 110 within the tip assembly 100. The staggered contact points facilitate direct connection and routing of electrode contact elements (not shown in FIG. 1) through the electrode assembly 104, as well as convenient attachment of the lead wires 110 for each respective electrode 116 through 122 as described below.

The lead wires 110 extend from an end 112 of the coupler portion 108, and a flexible sump tube 114 is provided which can be inserted, together with the tip assembly 100, in any hollow viscous organ. The sump tube 114 is sealingly engaged to the tip assembly 100 over the coupler portion 108 such that the coupler portion 108 and lead wires 110 extend through a lumen (not shown in FIG. 1) of the sump tube 114 to an electrical multi-channel connector (not shown) that can be plugged into the impedance spectrometer portion (not shown) of a known impedance spectroscopy system.

The electrodes 116 through 122 of the electrode assembly 104 function as ionic-current-to-electronic-current transducers, such as Ag/AgCl electrodes. It is appreciated, however, that other types of suitable electrodes could be used without departing from the spirit and scope of the invention. The electrodes 116 through 122 are formed substantially identically to one another, and the electrodes 116 through 122 are spaced equally apart from one another along the electrode assembly 104, and are separated by dielectric spacer elements 124, 126, and 128. The outer diameters of the tip 102 and the electrodes 116 through 122 are about the same as an outer diameter of the spacer elements 124 through 128 and further are about the same as the outer diameter of the sump tube 114 to ensure that a substantially continuous outer surface of the tip assembly is formed. The tip assembly 100 interfaces with the sump tube 114 at a shoulder 130 of the connector portion 106 at an end 132 of the sump tube to form a contiguous outer surface of the tip assembly 100 and the tube 114 which facilitates insertion of the tip assembly 100 and sump tube 114 into a patient with minimal discomfort.

A signal processing device associated with the spectroscopy system, such as an appropriately-programmed general purpose computer, processes a complex impedance spectrum sensed by the electrode assembly 104 to detect tissue damage in a patient. To monitor mucosal damage, a catheter including the tip assembly 100 is placed in one of a patient's hollow viscous organs, and current is injected by two of the electrodes 116 and 122 at a range of frequencies. The other two electrodes 118 and 120 measure the resulting voltage spectrum, which is subsequently processed and analyzed. The spectroscopy system is of the type described in U.S. Patent Application Publication US 2002/0013537, the disclosure of which is hereby incorporated by reference in its entirety.

While four electrodes 116 through 122 are illustrated in the exemplary embodiment, it is appreciated that only two of the four electrodes may be provided in an alternative embodiment without departing from the scope of the present invention. In a two electrode embodiment, each electrode would be used for both current source and voltage measurement. Additionally, in a two electrode embodiment, only one of the dielectric spacer elements 124 through 128 would be employed in between the two electrodes. It is further contemplated that more than four electrodes may be provided in still another embodiment.

Figure 2:
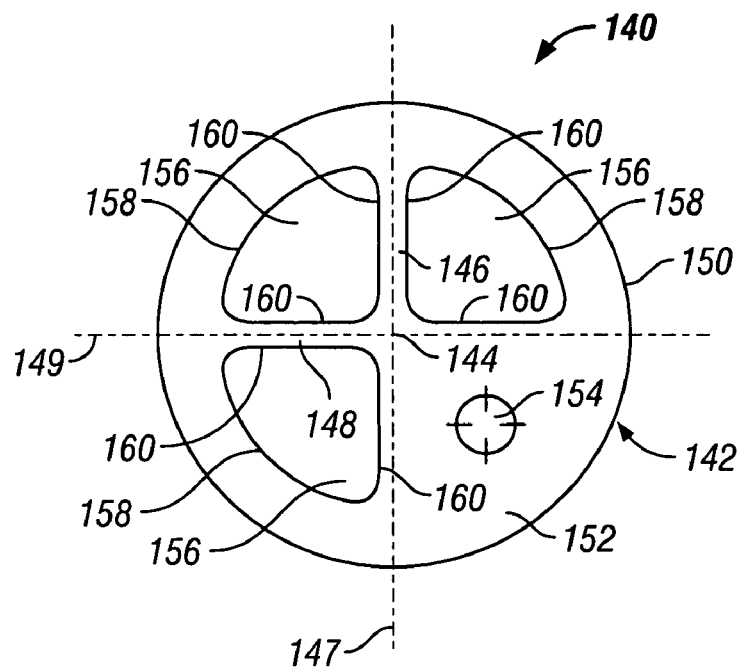
FIG. 2 is a top plan view of an exemplary electrode disk for the tip assembly shown in FIG. 1.

FIG. 2 is a top plan view of an exemplary electrode disk 140 which may be employed in the electrode assembly 104 (shown in FIG. 1) of the tip assembly 100 (shown in FIG. 1) as any of the electrodes 116, 118, 120 and 122 (all shown in FIG. 1). The disk 140 includes a body 142 having a center 144 corresponding to a central axis of the disk, two radially extending spokes 146 and 148 extending from the center 144, and a substantially cylindrical outer surface 150. The body 142 further includes substantially flat and parallel end planes or surfaces 152 (only one of which is visible in FIG. 2) which are perpendicular to the central axis. The spokes 146 and 148 extend substantially perpendicular to one another in one embodiment, and centerlines 147 and 149 through each of the spokes 146 and 148 intersect at the center 144 of the disk 140 and define four substantially equal regions or quadrants of the disk 140. A circular contact aperture 154 extends between the opposite end planes of surfaces 152 in one of the quadrants, and the remaining three quadrants each include a lead aperture 156. As illustrated in FIG. 2, each lead aperture 156 is significantly larger than the contact aperture 154, and each lead aperture 156 includes a curved edge 158 extending parallel to the cylindrical outer surface 150 and substantially straight edges 160 extending substantially parallel to one of the spokes 146 and 148. Each of the lead apertures 156 therefore has a rounded triangular shape or profile in an exemplary embodiment. It is recognized, however, that a variety of shapes of lead apertures 156 may be employed in further and/or alternative embodiments of the invention.

In use, and as further described below, a contact element 170 is positioned in the contact aperture 154. The contact element is attached to a respective wire lead 110 (shown in FIG. 1) as the tip assembly 100 (shown in FIG. 1) is manufactured. The lead apertures 156 facilitate passage of the contact element through the electrode assembly 104 (shown in FIG. 1) and further facilitates molding of the dielectric spacer elements 124, 126 and 128 (shown in FIG. 1) during fabrication of the tip assembly 100.

Figure 3:
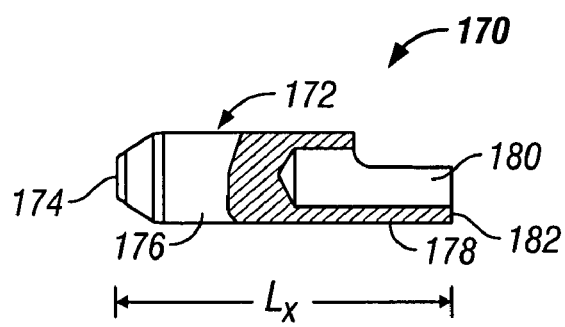
FIG. 3 is partial cross sectional plan view of an exemplary electrode contact for the tip assembly shown in FIG. 1.

FIG. 3 is partial cross sectional plan view of an exemplary electrode contact element 170 in the form of an elongated contact pin for the tip assembly 100 (shown in FIG. 1). In an exemplary embodiment, the contact pin 170 includes a body 172 having a tapered leading end 174, a substantially cylindrical shaft portion 176, and a hollow, cup like tail portion 178 forming a passage 180 which receives an end (not shown) of one of the lead wires 110 (shown in FIG. 1). In one embodiment, the tail portion 178 and the passage 180 form a solder cup for electrically connecting stripped conductors of a lead wire 110 via a known soldering process. It is appreciated, however, that other electrical connection techniques may be employed in lieu of soldering to establish an electrical connection between the contact pin 170 and a lead wire 110 in alternative embodiments.

The electrode assembly 104 according to the invention includes one contact pin 170 for each electrode in the assembly, and hence in the illustrated embodiment, the electrode assembly 104 includes four separate contact pins 170, and each contact pin 170 corresponds to one of the electrodes 116, 118, 120 and 122. In a two electrode embodiment, two contact pins 170 would be employed.

Figure 11:
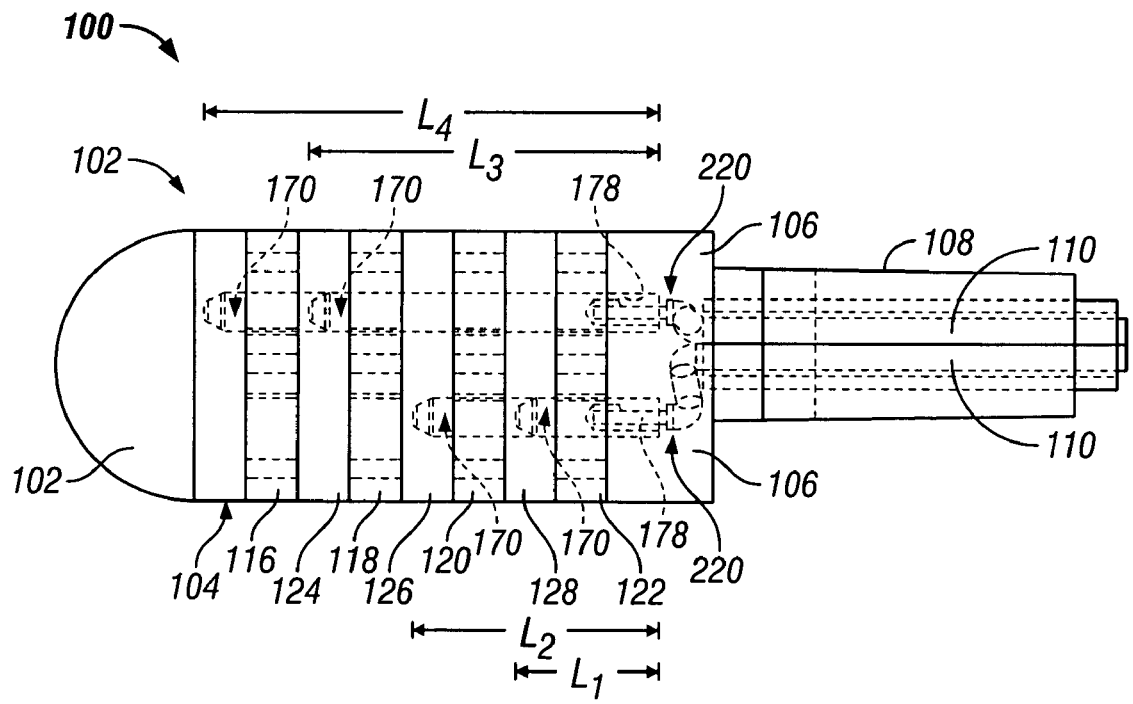
FIG. 11 is a schematic view of a completed catheter tip assembly.

The shaft portion 176 of each contact pin 170 is dimensioned for press fitting a contact pin 170 into the contact aperture 154 (shown in FIG. 2) of each electrode 116 through 122 (shown in FIG. 1), and hence in the illustrated embodiment, one contact pin 170 is press fit into the contact aperture 154 of each electrode 116 through 122. Each contact pin 170 has an axial length $L_x$ measured from a tip of the leading end 174 to an end 182 of the tail portion 178, and $L_x$ corresponds to an axial distance from a connection point 220 (shown in FIG. 11) in the connector portion 106 (shown in FIG. 11) of the tip assembly 100 to the respective electrode 116 through 122. That is, $L_x$ varies depending upon which electrode 116, 118, 120 or 122 the contact pin 170 engages in the electrode assembly 104. Referring, for example, to FIG. 11, from the shortest contact length $L_x$ to the longest contact length $L_x$ in a four electrode embodiment, the first electrode 122 closest to the connection point 220 has a length $L_1$, the next closest electrode 120 has a length $L_2$, the next closest electrode 118 has a length $L_3$, and the farthest electrode 116 has a length $L_4$. Comparing FIG. 11 and FIG. 3, it may be seen that the difference in length $L_x$ of the contact pins 170 is principally the different length of the shaft portions 176 of the contact pins 170.

By engaging the contact pins 170 to the contact apertures 154 of the electrodes 116 through 122, and further by stacking and rotating the electrodes as described below, reliable electrical connection may be established between the respective electrodes 116 through 122, the contact pins 170 and the lead wires 110 (shown in FIG. 1).

Figure 4:
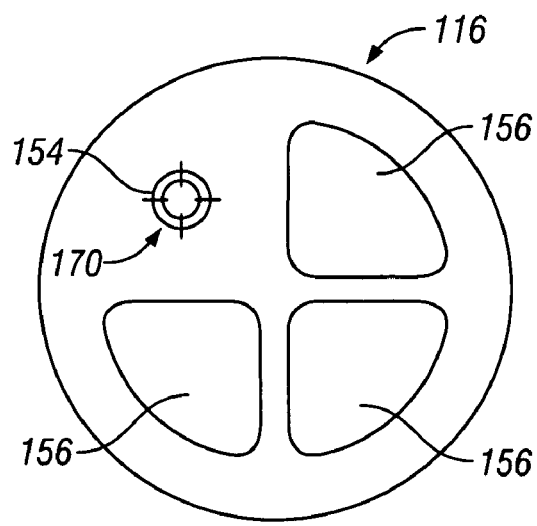
FIG. 4 is a top plan view in a first stacked position of an electrode assembly for the tip assembly shown in FIG. 1.

FIGS. 4–7 illustrate a stacking and rotating procedure for fabricating the electrode assembly 104 (shown in FIG. 1). FIG. 4 shows the electrode 116 having a press fit contact pin 170 engaged to contact aperture 154. The lead openings 156 of the electrode 116 are open and clear of any contact pins 170.

Figure 5:
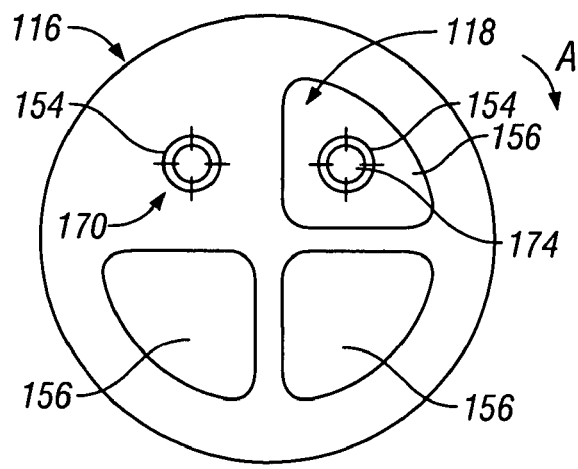
FIG. 5 is a top plan view of the electrode assembly in a second stacked position.

FIG. 5 illustrates the electrode 116 and the electrode 118 in a stacked relation, with the electrode 118 situated underneath and substantially axially aligned with the electrode 116. That is, the centers 144 (shown in FIG. 2) of each of the electrodes 116 and 118 are substantially aligned along a common axis. The electrode 118 is rotated 90 degrees in the direction of arrow A about the center axis relative to the electrode 116. As such, the contact aperture 154 of the electrode 118 is located beneath one of the lead apertures 156 of the electrode 116, and the leading end 174 of a contact pin 170 engaged to the electrode 118 is positioned generally 90 degrees about the center axis from the contact aperture 154 of the electrode 116. The lead apertures 156 on the lower portion of the electrodes 116 and 118 in FIG. 5 are substantially aligned with one another, and the contact pin 170 coupled to the electrode 116 extends through the remaining lead aperture 156 (not visible in FIG. 5) positioned underneath the contact aperture 154 of the electrode 116.

Figure 6:
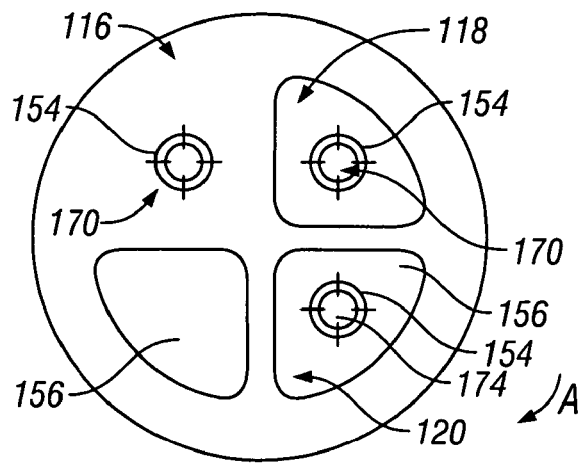
FIG. 6 is a top plan view of the electrode assembly in a third stacked position.

FIG. 6 illustrates the electrode 116, the electrode 118, and the electrode 120 in a stacked relation, with the electrode 120 situated underneath and substantially axially aligned with the electrodes 116 and 118. That is, the centers 144 (shown in FIG. 2) of each of the electrodes 116, 118, and 120 are substantially aligned along a common axis. The electrode 120 is rotated 90 degrees from the electrode 118 in the direction of arrow A about the center axis of the electrodes 116 and 118. As such, the contact aperture 154 of the electrode 120 is located beneath one of the lead apertures 156 of the electrode 118, and the leading end 174 of a contact pin 170 engaged to the electrode 118 is positioned generally 90 degrees about the center axis from the contact aperture 154 of the electrode 118. The lead apertures 156 on the lower left hand portion of the electrodes 116, 118, and 120 in FIG. 6 are substantially aligned with one another. The contact pin 170 coupled to the electrode 116 extends through lead apertures 156 (not visible in FIG. 6) of each of the electrodes 118 and 120 positioned underneath the contact aperture 154 of the electrode 116. The contact pin 170 coupled to the electrode 118 extends through one of the lead apertures 156 (not visible in FIG. 6) of the electrode 120 positioned underneath the contact aperture 154 of the electrode 118.

Figure 7:
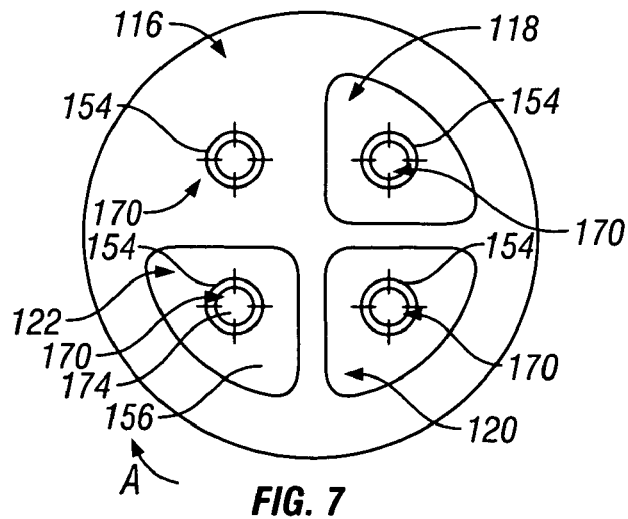
FIG. 7 is a top plan view of the electrode assembly in a fourth position.

FIG. 7 illustrates the electrodes 116, 118, 120 and 122 in a stacked relation, with the electrode 122 situated underneath and substantially aligned with the electrodes 116, 118 and 120. That is, the centers 144 (shown in FIG. 2) of each of the electrodes 116, 118, 120 and 122 are substantially axially aligned along a common axis. The electrode 122 is rotated 90 degrees from the electrode 120 in the direction of arrow A about the center axis of the electrodes 116, 118 and 120. As such, the contact aperture 154 of the electrode 122 is located beneath one of the lead apertures 156 of the electrode 120, and the leading end 174 of a contact pin 170 engaged to the electrode 120 is positioned generally 90 degrees about the center axis from the contact aperture 154 of the electrode 120. The contact pin 170 coupled to the electrode 116 extends through lead apertures 156 (not visible in FIG. 7) of each of the electrodes 118, 120 and 122 positioned underneath the contact aperture 154 of the electrode 116. The contact pin 170 coupled to the electrode 118 extends through the lead apertures 156 (not visible in FIG. 7) of the electrodes 120 and 122 positioned underneath the contact aperture 154 of the electrode 118. The contact pin 170 coupled to the electrode 120 extends through the lead aperture 156 (not visible in FIG. 7) of the electrode 122 positioned underneath the contact aperture 154 of the electrode 120.

In the stacked orientation of FIG. 7, the electrode assembly 104 may be secured together in a molding process. The contact pins 170 of the respective electrodes 116 through 122 are positioned 90 degrees about the center axis from one another in the stack, and the contact pins 170 extend through the lead apertures 156 of subsequent electrodes in the stack. The stacked electrodes 116 through 122 and associated contact pins 170 may be placed in a mold (not shown) and the stack is overmolded with a dielectric material according to a known process to form the tip 102 (shown in FIG. 1) and the spacer elements 124, 126 and 128 (shown in FIG. 1). In one embodiment, the outer surfaces 150 of the electrodes 116 through 122 are secured in the mold within pockets or channels in the mold, and the dielectric material flows through the lead apertures 156 and between the respective electrodes 116, 118 and 120, thereby forming an integral electrode assembly 104 wherein the dielectric spacer elements 124, 126, and 128 are intimately formed with the stacked electrodes 116 through 122 and the associated contact pins 170.

Figure 8:
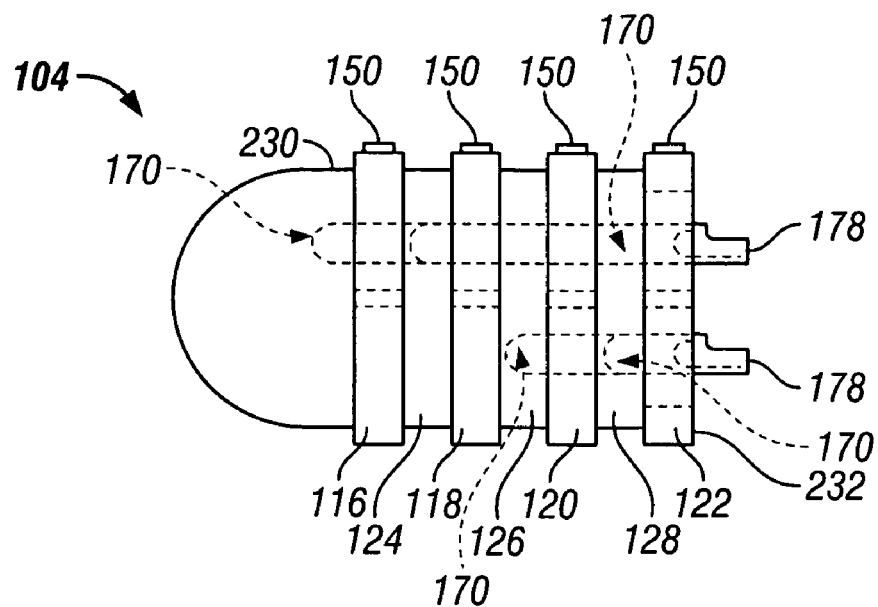
FIG. 8 illustrates the electrode assembly at another stage of manufacture.

FIG. 8 illustrates the electrode assembly 104 at a stage of manufacture just after overmolding of the stacked and rotated electrodes 116 through 122. The outer surface 150 of each of the electrodes 116 through 122 extends beyond an outer surface 230 of the molded tip 102 and the dielectric spacer elements 124 through 128 due to the configuration of the mold. The rounded tip 102 is molded on one end of the electrode assembly 104 adjacent the electrode 116, and the tail portions 178 of the contact pins 170 extend from an opposite end 232 of the electrode assembly 104 proximate the electrode 122. The respective tail portions 178 of each of the contact pins 170 connected to each of the electrodes 116, 118, 120 and 122 are therefore exposed for connecting the lead wires 110 (shown in FIG. 1) to the contact pins 170.

Figure 9:
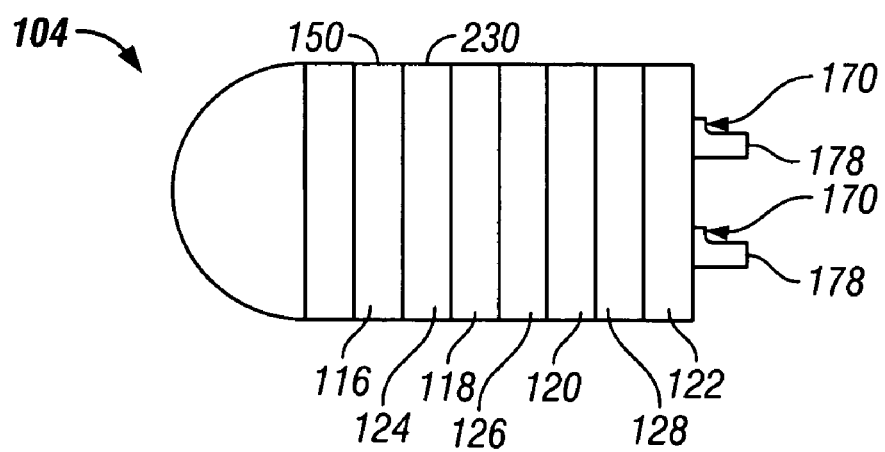
FIG. 9 illustrates the electrode assembly at a further stage of manufacture.

FIG. 9 illustrates the electrode assembly 104 at a subsequent stage of manufacture wherein the outer surfaces 150 of the electrodes 116, 118, 120, and 122 are machined such that the outer surfaces 150 of the electrodes, together with the outer surfaces 230 of the dielectric spacer elements 124, 126 and 128, form a substantially smooth and continuous outer surface over the integral electrode assembly 104. The lead wires 110 (shown in FIG. 1) are connected to each of the exposed respective tail portions 178 of the contact pins 170 by, for example, a known soldering process.

After the lead wires 110 are attached to the contact pins 170, the electrode assembly 104 is placed in a mold, and the connector portion 106 (shown in FIG. 1) and the coupler portion 108 (also shown in FIG. 1) are overmolded to form the tip assembly 100 (shown in FIG. 1).

Figure 10:
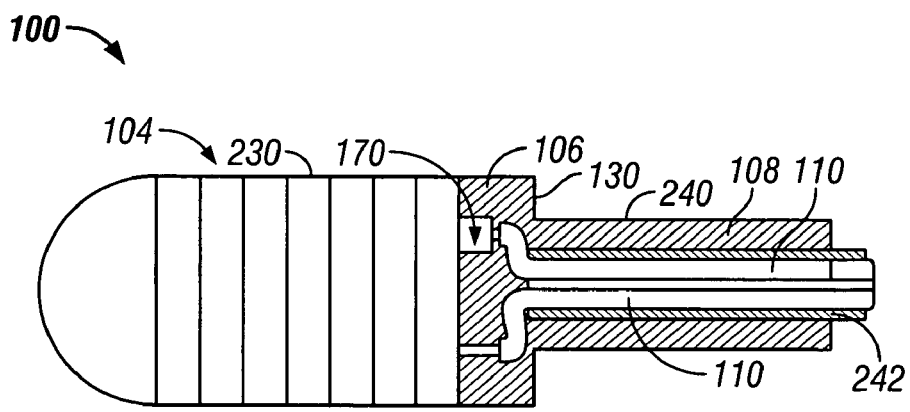
FIG. 10 is a partial cross sectional view of the catheter tip assembly at a final stage of manufacture.

FIG. 10 is a partial cross sectional view of the tip assembly 100 after the electrode assembly 104 is overmolded to form the connector portion 106 which encases the soldered contact pins 170 and the coupler portion 108 which extends over the lead wires 110. The coupler portion 108 extends from a shoulder 130 at the end of the connector portion 106 which forms a step between the outer surface 230 of the electrode assembly 104 and an outer surface 240 of the coupler portion 108. The lead wires 110 are gathered together and extend through a central passage 242 in the coupler portion 108. The passage 242 is dimensioned to receive the wires 110 corresponding to each of the contact pins 170 in the electrode assembly 104.

FIG. 11 is a schematic view of a completed tip assembly 100. Each of the electrodes 116 through 122 are electrically connected to one of the respective contact pins 170 within the respective contact apertures 154 and extending for axial lengths $L_1$ through $L_4$ in the electrode assembly 104. The dielectric spacer elements 124, 126 and 128, and also the tip 102 are molded over the electrodes 118 through 122. The wire leads 110 are coupled to the respective tail portions 178 of each of the contact pins 170, and the connector portion 106 and the coupler portion 108 are molded over the contact points 220 and the lead wires 110 to complete the assembly 100.

Summarizing, the assembly 100 is fabricated by pressing fitting the contact pins 170 to the electrodes 116 through 122; stacking and rotating the electrodes 116 through 122 and the associated contact pins 170 with the contact pins 170 axially offset from one another and extending through lead apertures 156 (shown in FIGS. 2 and 4–7) of subsequent electrodes in the stack; overmolding the stacked electrodes to form the tip 102 and the dielectric spacer elements 124, 126, and 128 as illustrated in FIG. 8; machining the electrodes to form a smooth and continuous outer surface on the electrode assembly 104 as shown in FIG. 9; connecting the lead wires 110 to the tail portions 178 of the electrode assembly; and overmolding the electrode assembly 104 and the lead wires to form the connector portion 106 and the coupler portion 108. Once completed, the tip assembly 100 may be tested to ensure proper operation of the electrode assembly 104 before use.

The above described tip assembly 100 and method of fabrication provides a number of advantages over known tip assembly constructions. For example, the staged molding of the tip assembly to form the dielectric spacer elements 124, 126 and 128 and the connector and coupler portions 106 and 108 eliminates separately provided components and reduces the number of parts in the tip assembly. The substantially identically formed electrodes may be manufactured in bulk, and the contact pins 170 are of a uniform design albeit different lengths. Rotating the electrodes 116 through 122 and providing the contact pins 170 avoids difficulties in connecting the electrodes to the lead wires 110, thereby reducing assembly time and costs. Reliable and consistent electrical connections for the electrodes 116 through 122 are therefore achieved in a relatively low cost and straightforward manufacturing process.

Figure 12:
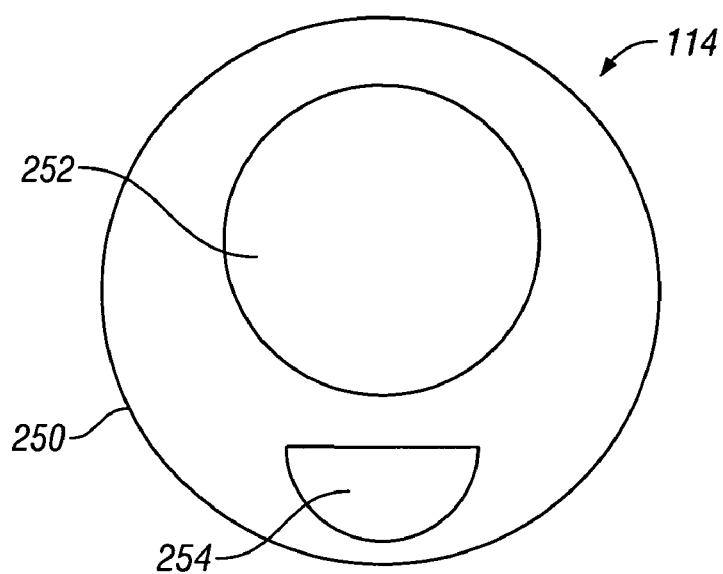
FIG. 12 is a sectional view of an exemplary sump tube for the tip assembly shown in FIGS. 1 and 11.

FIG. 12 is a sectional view of an exemplary sump tube 114 for the tip assembly 100 (shown in FIG. 11). In one embodiment, the sump tube 114 includes a cylindrical outer surface 250 having an outer diameter substantially equal to an outer diameter of the electrode assembly 104 (shown in FIG. 11), a first passage or lumen 252 extending through the tube 114, and a second lumen 254 extending through the tube 114. The first lumen 252 is substantially a cylindrical passage having a complementary shape to the coupler portion 108 (shown in FIG. 11) of the tip assembly 100 and dimensioned to receive the coupler portion 108 therein. The lumen 252 is inserted over the coupler portion 108 and the tube 114 is sealed to the coupler portion 108 at one end thereof. The lead wires 110 extend through the lumen 252 and are connected to external equipment on an opposite end for transmitting and receiving signals to and from the electrodes. It is recognized that the coupler portion 108 and the lumen 252 may be formed into a variety of alternative complementary shapes in lieu of a cylindrical shape in alternative embodiments.

The second lumen 254, sometimes referred to as a primary lumen, is provided for feeding/sump tube purposes or as another type of life support. When placed in fluid communication with an organ, the primary lumen 254 may be used, for example, for passage of food to a patient, for drainage of fluid from the patient, or other purposes. It is appreciated that the primary lumen 254 may have a variety of shapes in various embodiments.

Figure 13:
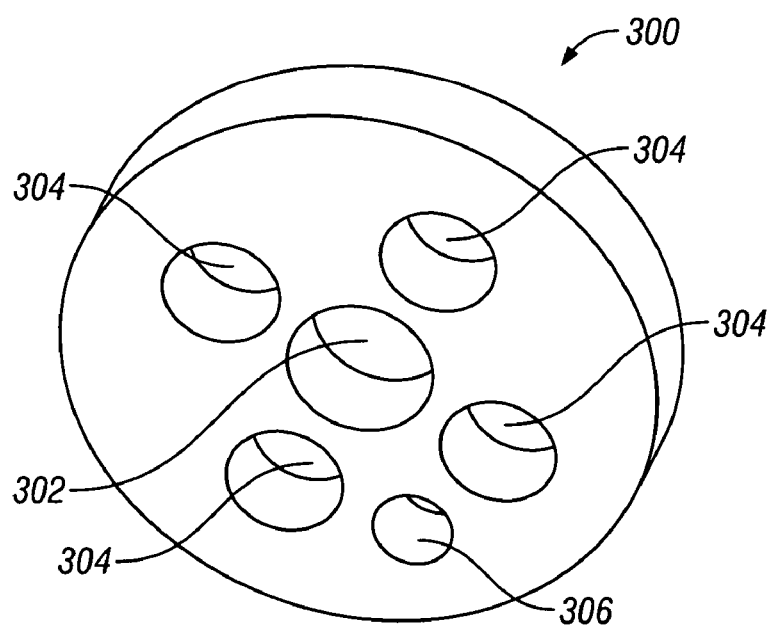
FIG. 13 is a perspective view of an exemplary electrode disk formed in accordance with another exemplary embodiment of the present invention.

FIG. 13 is a perspective view of an exemplary electrode disk 300 formed in accordance with another exemplary embodiment of the present invention and which may be used to construct a tip assembly (not shown in FIG. 12) according to another method. The electrode 300 includes a central aperture 302, four substantially equally spaced contact apertures 304 positioned around the central aperture 302, and one positioning aperture 306 located between two of the contact apertures 304. The electrode 300 functions as an ionic-current-to-electronic-current transducer, such as an Ag/AgCl electrode, although it is appreciated that another type of suitable electrode could be used without departing from the spirit and scope of the invention.

Figure 14:
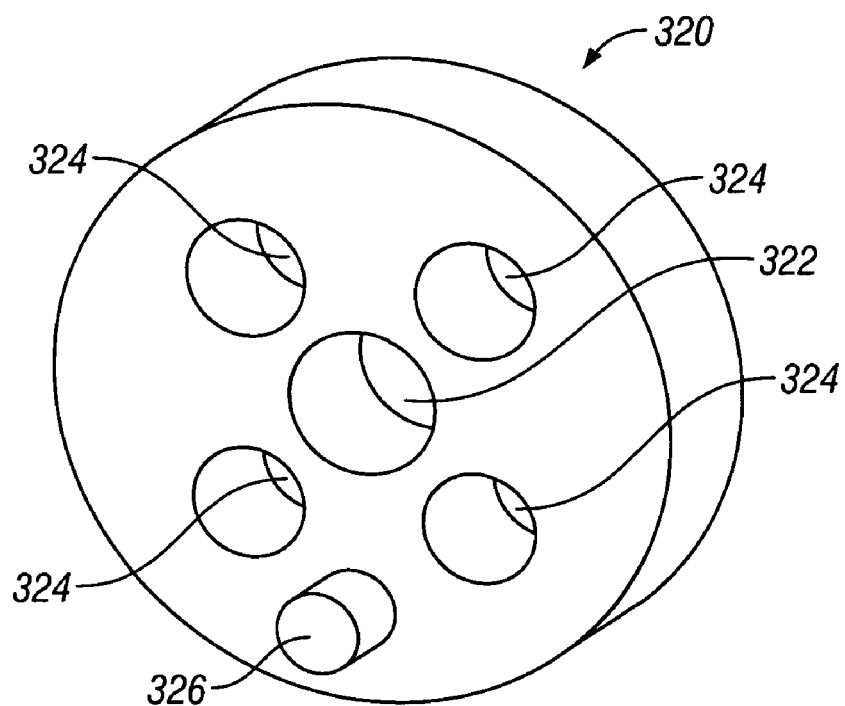
FIG. 14 is a perspective view of a dielectric spacer element for use with the electrode disk shown in FIG. 13.

FIG. 14 is a perspective view of a dielectric spacer element 320. The spacer element 320 includes a central aperture 322, four substantially equally spaced contact apertures 324 positioned around the central aperture 322, and one positioning protrusion or peg 326 located between two of the contact apertures 324. The peg 326 is dimensioned for press fit insertion into the positioning aperture 306 (shown in FIG. 13) of the electrode 300 to mate the electrode 300 to the spacer element 320. The spacer element 320 is fabricated from a dielectric material according to known processes and techniques.

Figure 15:
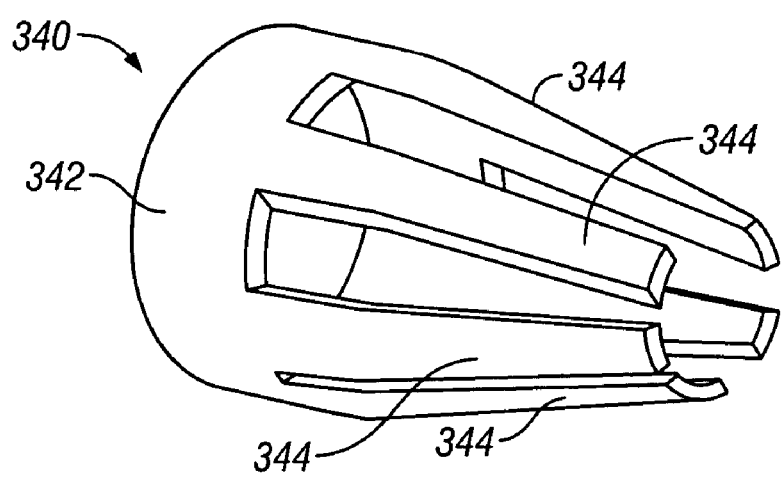
FIG. 15 is a perspective view of an exemplary contact clip for use with the electrode and dielectric disk shown in FIGS. 13 and 14.

FIG. 15 is a perspective view of an exemplary contact element in the form of a contact clip 340 including a rim 342 and a number of inclined contact fingers 344 extending from the rim 342 and converging toward one another. The rim 342 is dimensioned for press fit insertion into one of the contact apertures 304 of the electrode 300 (shown in FIG. 13) with the contact fingers 344 extending from one side of the electrode 300. The contact clip 340 may be fabricated from a conductive material according to known techniques.

Figure 16:
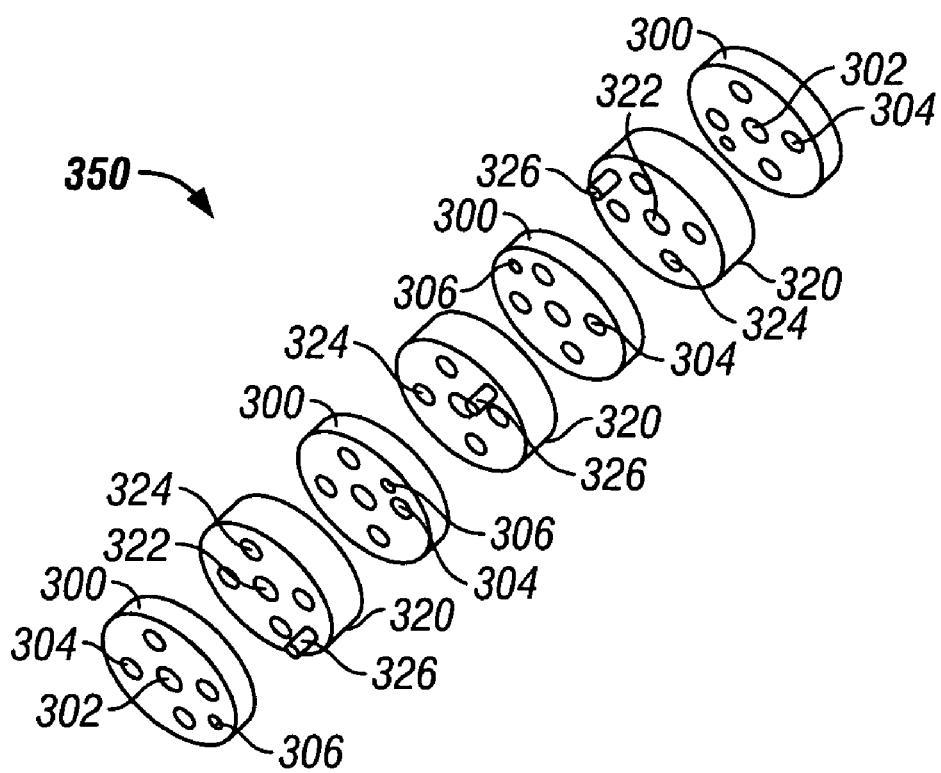
FIG. 16 is an exploded view of an electrode assembly at a first stage of manufacture.

FIG. 16 is an exploded view of an electrode assembly 350 at a first stage of manufacture wherein a number of electrodes 300 are stacked with dielectric spacer elements 320 sandwiched between the electrodes. A positioning peg 326 of a spacer 320 is inserted into the positioning aperture 306 of the adjacent electrode 300, and each of the electrodes 300 is rotated about 90 degrees about the center axis from the adjacent electrode 300 in the stack. The respective spacer elements 320 are accordingly rotated so that the pegs 326 may be engaged to the respective electrodes 300. The contact apertures 304 and 324 of the electrodes 300 and the spacer elements 320 are substantially aligned with the adjacent electrodes/spacer elements to form contact passages through the stack. The central apertures 302 and 322 of the electrodes 300 and the spacer elements 320 are substantially aligned with the adjacent electrodes/spacer elements to form a continuous center passage through the stack.

A contact clip 340 (shown in FIG. 15) is inserted into each of the electrodes 300 in one of the contact apertures 304 such that, when the electrodes are stacked and rotated, the contact clips 340 are positioned 90 degrees from one another within the stack. The contact fingers 344 of the clips 340 extend through the contact apertures 324 of adjacent spacer elements 320.

Figure 17:
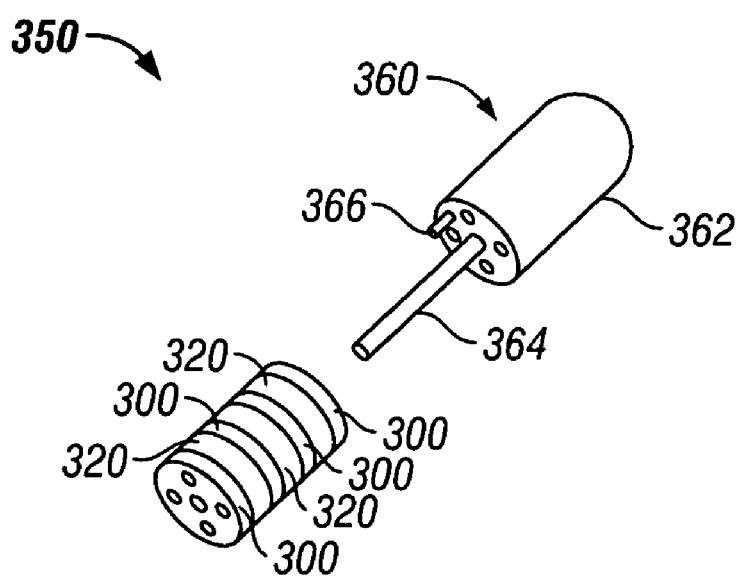
FIG. 17 is an exploded view of the electrode assembly shown in FIG. 16 at a second stage of manufacture.

FIG. 17 is a view of the electrode assembly 350 at a second stage of manufacture wherein a separately formed tip 360 is provided having a rounded head 362, a central post 364 extending therefrom, and a positioning peg 366. The post 364 is inserted through the central apertures 302 and 322 of the electrodes 300 and the spacer elements 320, and the peg 366 is inserted into the positioning aperture 306 in the adjacent electrode 300. Once the tip 360 is coupled to the electrode assembly 350, the electrode assembly 350 may be placed in a mold and overmolded to form a connector portion (not shown in FIG. 17) on an end of the electrode assembly 350 opposite the tip 360.

Figure 18:
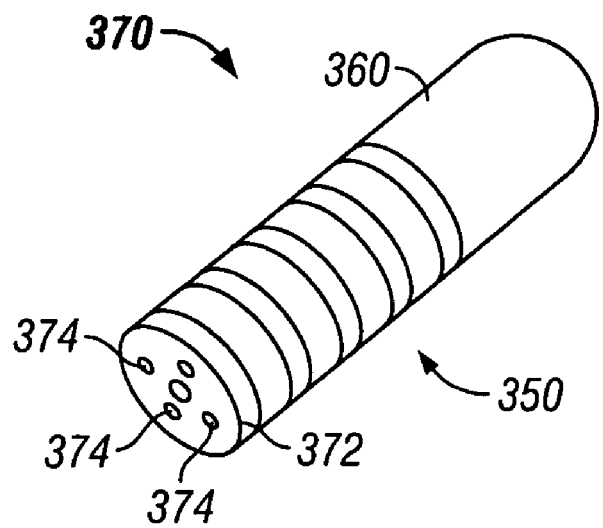
FIG. 18 is a perspective view of the electrode assembly shown in FIG. 16 at a third stage of manufacture.

FIG. 18 is a perspective view of a tip assembly 370 after the electrode assembly 350 is molded to form a connector portion 372. The connector portion includes contact apertures 374 extending through the connector portion 372 and aligning with the contact apertures of the electrode assembly 350. The post 364 (shown in FIG. 17) of the tip 360 is in intimate contact with and secured to the connector portion 374 to hold the tip assembly together.

Figure 19:
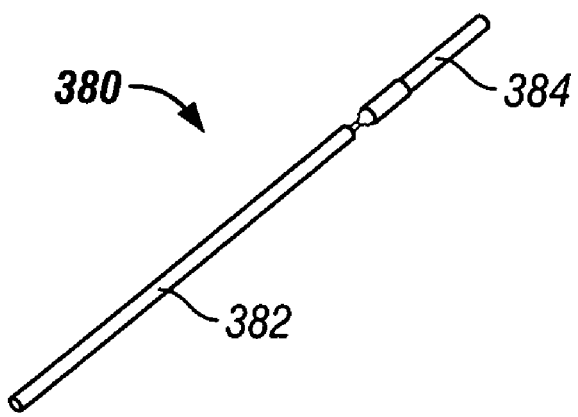
FIG. 19 illustrates an exemplary lead wire and contact for the electrode assembly shown in FIG. 18.

FIG. 19 illustrates an exemplary lead wire and contact assembly 380 including a lead wire 382 and a contact 384 which is crimped to the conductors of the wire 384. The contacts 384 are shaped for engagement with the fingers 344 (shown in FIG. 15) of the contact clips 340 (shown in FIG. 15).

Figure 20:
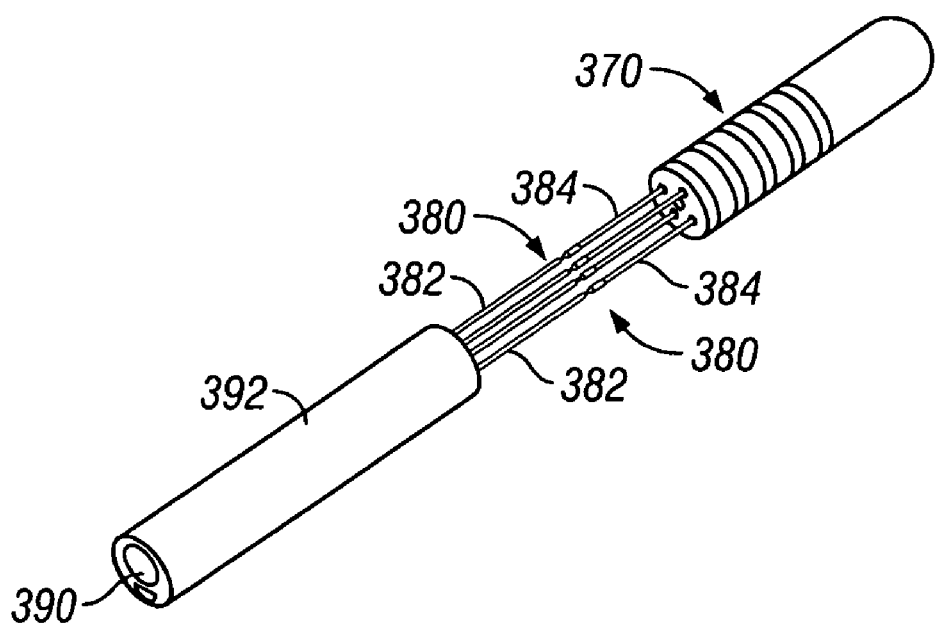
FIG. 20 is an assembly view of the electrode assembly shown in FIGS. 16–18 at a fourth stage of manufacture.

FIG. 20 is a perspective view of a number of wire and contact assemblies 380 extended through a lumen 390 of a flexible tube 392, and the contacts 384 inserted into the contact apertures of the tip assembly 370. The wires 382 are inserted into the tip assembly 370 until the respective contact 384 engages one of the contact clips 340 in the electrode assembly 350.

Figure 21:
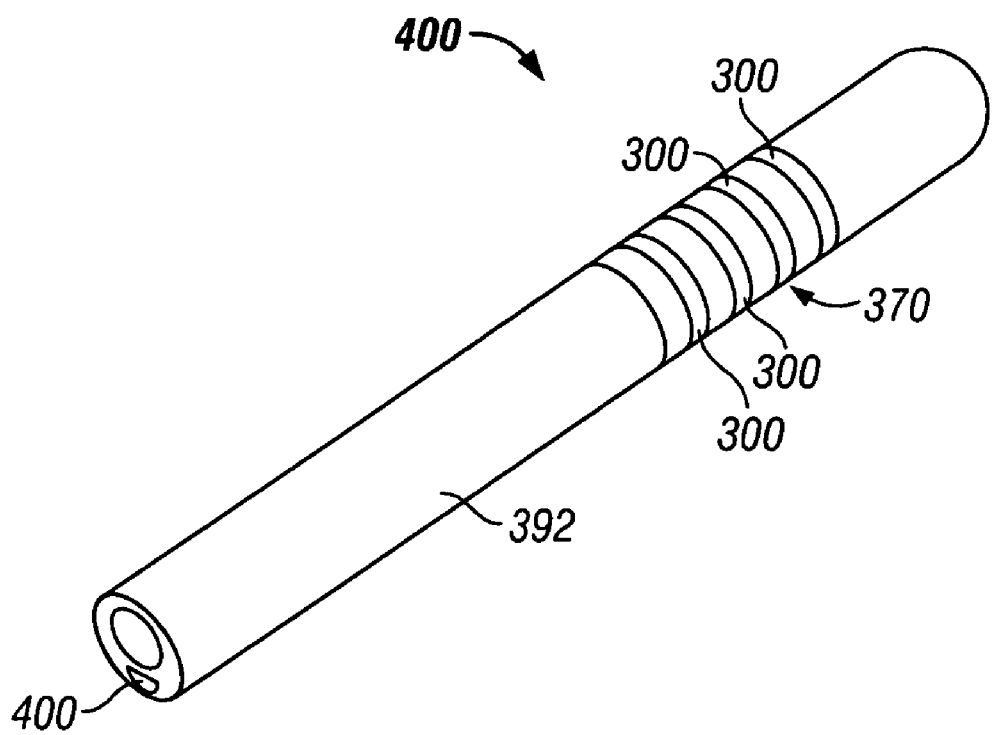
FIG. 21 is a perspective view of a completed electrode assembly.

FIG. 21 illustrates a completed catheter assembly 400 including the tip assembly 370 and the tube 392 coupled thereto. A second lumen 400 is provided in the tube as desired. The lead wires 382 extend through the first lumen 390 of the tube 392 and to external equipment to transmit and receive signals from the electrodes 300.

Summarizing, the assembly 370 is fabricated by pressing fitting the contact clips 340 to the electrodes 300; rotating the electrodes 300 and the associated contact clips 340 with the contact clips 340 offset from one another and extending through the contact apertures 324 of the spacer elements 320 in the stack; stacking the electrodes 300 and the spacer elements 320 such that the dielectric spacer elements 320 are sandwiched between the electrodes 300; inserting a tip 360 into the stacked electrodes; overmolding the stacked electrodes to form the connector portion 372 and to secure the stack to the tip 360; crimping the contacts 384 to the lead wires 382; and inserting the lead wires 382 into the contact apertures in the stack until the contacts engage the contact clips 340. Once completed, the tip assembly 370 may be tested to ensure proper operation of the electrode assembly 350 before use.

The above described tip assembly 370 and method of fabrication provides a number of advantages over known tip assembly constructions. For example, the substantially identically formed electrodes and spacer elements may be manufactured in bulk at a relatively low cost. Rotating the electrodes and providing the contact clips avoids difficulties in connecting the electrodes to the lead wires, and engaging the crimped contacts to the contact clips is easily accomplished. Reliable and consistent electrical connections for the electrodes are therefore achieved in a relatively low cost and straightforward manufacturing process.

While the invention has been described in terms of various specific embodiments, those skilled in the art will recognize that the invention can be practiced with modification within the spirit and scope of the claims.

What is claimed is:

1. An electrode assembly for a sensor catheter tip, said assembly comprising:
   a first electrode and a second electrode, each electrode comprising a body having a center axis and a contact aperture radially spaced from the center axis, the electrodes being axially aligned and spaced apart along the axis; and
   a first contact element and a second contact element positioned within each said contact aperture in the respective first electrode and second electrode, each of the first and second contact elements configured to receive a wire lead and establish electrical contact with the respective first and second electrodes;
   wherein said first and second contact elements are radially offset from one another, thereby providing staggered contact points for each respective electrode;
   wherein each of said contact elements have an axial length, said axial length of said contacts being different from one another.

2. An electrode assembly in accordance with claim 1 wherein said first and second contact elements are offset approximately 90 degrees from one another.

3. An electrode assembly in accordance with claim 1 wherein each of said first and second electrodes further comprise a lead aperture spaced from said contact aperture and also radially spaced from the center axis, said lead apertures of said first and second electrodes being substantially aligned with one another.

4. An electrode assembly in accordance with claim 1 wherein said assembly further comprises a dielectric spacer element disposed between said first and second electrodes, said dielectric spacer element extending at least partially through one of said electrodes.

5. An electrode assembly in accordance with claim 1 further comprising an injection molded dielectric spacer element positioned between said electrodes.

6. An electrode assembly in accordance with claim 1 wherein said first and second electrodes are substantially identically formed.

7. An electrode assembly for a sensor catheter tip, said assembly comprising:
   a first electrode and a second electrode, each electrode comprising a body having a center axis and a contact aperture radially spaced from the center axis, the electrodes being axially aligned and spaced apart along the axis; and
   a first contact element and a second contact element positioned within each said contact aperture in the respective first electrode and second electrode, each of the first and second contact elements configured to receive a wire lead and establish electrical contact with the respective first and second electrodes;
   wherein said first and second contact elements are radially offset from one another, thereby providing staggered contact points for each respective electrode;
   wherein each of said first and second electrodes comprise a disk having intersecting spokes defining substantially equal regions on each disk, said contact element positioned in one of said regions, the other of said regions comprising a lead aperture extending therethrough.

8. An electrode assembly in accordance with claim 1 wherein said contact element comprises a tail portion configured for soldering.

9. A catheter tip assembly for an impedance spectroscopy system, said assembly comprising:
   a rounded dielectric tip;
   a first electrode disk adjacent said tip, said first electrode disk comprising a body having a contact aperture therethrough;
   a second electrode disk axially spaced from said first electrode disk, said second electrode comprising a body having a contact aperture therethrough;
   wherein said second electrode disk is rotated relative to said first electrode disk about a longitudinal axis so that said contact apertures are circumferentially offset from one another; and
   first and second contact elements each adapted for press fit insertion into the respective first and second electrode disks on a first end and adapted to engage a lead wire on another end opposite the first end;
   wherein each of the first and second electrode disks comprise a plurality of lead apertures spaced from the contact apertures in each respective disk, and one of said first and second contact elements extending through one of the lead apertures in one of said first and second electrode disks.

10. A catheter tip assembly in accordance with claim 9 further comprising a third electrode disk and a fourth electrode disk, said third and fourth electrode disks substantially identical to said first and second electrode disks;
   wherein each of said first, second, third and fourth electrode disks are circumferentially rotated relative to one another.

11. A catheter tip assembly in accordance with claim 9, each of said first and second contact elements have a different axial length.

12. A catheter tip assembly in accordance with claim 9 further comprising a dielectric spacer element sandwiched between said first and second electrodes.

13. A catheter tip assembly in accordance with claim 9 further comprising a connector portion on an end of said tip assembly opposite said tip, each of the first and second contact elements terminated to a lead wire within said connector portion.

14. A catheter tip assembly in accordance with claim 9 further comprising a coupler portion configured for attachment to a sump tube.

15. A catheter tip assembly in accordance with claim 9, wherein at least one of said first and second electrodes comprises a spoke, and said contact aperture being spaced from said spoke.

16. An electrode assembly for a sensor catheter tip, said assembly comprising:
   a first electrode and a second electrode, each electrode comprising a body having a center axis and a contact aperture radially spaced from the center axis, the electrodes being axially aligned and spaced apart along the axis; and
   a first contact element and a second contact element positioned within each said contact aperture in the respective first electrode and second electrode, each of the first and second contact elements configured to receive a wire lead and establish electrical contact with the respective first and second electrodes;
   wherein said first and second contact elements are radially offset from one another, thereby providing staggered contact points for each respective electrode;
   wherein at least one of said first and second electrodes comprises a spoke, and said contact aperture being spaced from said spoke.

* * * * *